(12) United States Patent
Elbert et al.

(10) Patent No.: US 9,822,251 B2
(45) Date of Patent: Nov. 21, 2017

(54) ANTI YELLOWING COMPOSITION

(75) Inventors: Bernhard Elbert, Stade (DE); Eike Jahnke, Frankfurt (DE)

(73) Assignee: TRINSEO EUROPE GMBH, Horgen (CH)

( * ) Notice: Subject to any disclaimer, the term of this patent is extended or adjusted under 35 U.S.C. 154(b) by 0 days.

(21) Appl. No.: 14/343,130

(22) PCT Filed: Aug. 28, 2012

(86) PCT No.: PCT/EP2012/066666
§ 371 (c)(1),
(2), (4) Date: May 12, 2014

(87) PCT Pub. No.: WO2013/034464
PCT Pub. Date: Mar. 14, 2013

(65) Prior Publication Data
US 2015/0159014 A1    Jun. 11, 2015

(30) Foreign Application Priority Data

Sep. 8, 2011    (EP) .................................... 11180524

(51) Int. Cl.
| | | |
|---|---|---|
| *C08L 69/00* | (2006.01) | |
| *C08K 5/053* | (2006.01) | |
| *C08K 5/10* | (2006.01) | |
| *A61L 2/08* | (2006.01) | |
| *C08K 5/372* | (2006.01) | |
| *A61L 31/04* | (2006.01) | |
| *A61L 31/14* | (2006.01) | |
| *C09K 15/12* | (2006.01) | |
| *C08L 71/02* | (2006.01) | |

(52) U.S. Cl.
CPC ............... *C08L 69/00* (2013.01); *A61L 2/081* (2013.01); *A61L 31/041* (2013.01); *A61L 31/14* (2013.01); *C08K 5/372* (2013.01); *C09K 15/12* (2013.01); *A61L 2/08* (2013.01); *C08L 71/02* (2013.01); *C08L 2201/08* (2013.01); *C08L 2203/02* (2013.01)

(58) Field of Classification Search
CPC ....... C08L 69/00; C08K 5/0059; C08K 5/053; C08K 5/37

USPC .................................................. 524/307, 386
See application file for complete search history.

(56) References Cited

U.S. PATENT DOCUMENTS

| | | | |
|---|---|---|---|
| 3,360,499 A | | 12/1967 | Mauz et al. |
| 3,362,932 A | | 1/1968 | Mauz et al. |
| 4,303,759 A | * | 12/1981 | Dixon et al. .................. 524/167 |
| 4,904,710 A | * | 2/1990 | Nace ............................. 523/137 |
| 4,939,185 A | * | 7/1990 | Nelson et al. ................ 523/136 |
| 5,464,893 A | | 11/1995 | Archey et al. |
| 5,852,070 A | * | 12/1998 | Ebert et al. .................... 523/136 |
| 2003/0186955 A1 | * | 10/2003 | Vange .................... A01N 43/50 514/184 |
| 2007/0292305 A1 | * | 12/2007 | Dempsey et al. .............. 422/28 |
| 2009/0088514 A1 | * | 4/2009 | Shiping ........................ 524/451 |

FOREIGN PATENT DOCUMENTS

| | | |
|---|---|---|
| EP | 0 152 012 | 8/1985 |
| EP | 0 228 525 | 7/1987 |
| EP | 0 611 797 | 8/1994 |
| EP | 0 778 312 | 6/1997 |
| GB | 1052968 | 12/1966 |
| GB | 1072224 | 6/1967 |
| JP | S44945 | 1/1969 |
| JP | S4852845 | 7/1973 |
| JP | H 0249048 | 2/1990 |
| JP | 2006-199846 | 8/2006 |

OTHER PUBLICATIONS

PCT/EP2012/066666 International Search Report dated Nov. 27, 2012 (3 pages).

* cited by examiner

*Primary Examiner* — Tae H Yoon
(74) *Attorney, Agent, or Firm* — Eric D. Babych; Brinks Gilson & Lione

(57) ABSTRACT

The present invention relates to a radical scavenging and anti-yellowing composition for polymeric materials and compositions containing the same. The invention further relates to medical devices comprising a composition according to the invention and to a method of sterilizing such devices.

3 Claims, 2 Drawing Sheets

ANTI YELLOWING COMPOSITION

Figure 1:
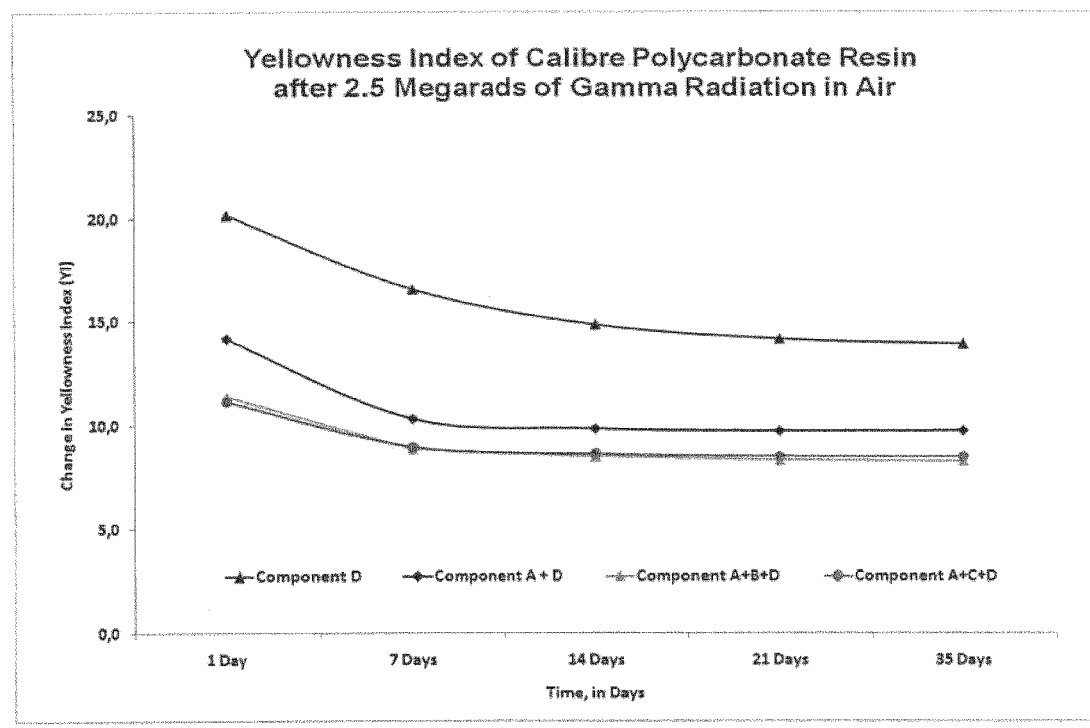

This application claims priority to International Application No. PCT/EP2012/066666 filed Aug. 28, 2012 and to European Application No. 11180524.8 filed Sep. 8, 2011, the entire contents of each are incorporated herein by reference.

The present invention relates to a radical scavenging and anti-yellowing composition for polymeric materials and compositions containing the same. The invention further relates to medical devices comprising a composition according to the invention and to a method of sterilizing such devices.

Polymeric materials find use in many articles, including articles for use in the medical field. Such articles frequently need to be sterilized. One common way of sterilizing polymeric articles for medical use is to expose the article to actinic radiation such as gamma radiation. In the context of sterilising articles, one typically also speaks of "ionising" or "high energy" radiation.

The high energy or actinic radiation produces free radicals in the polymeric material. The impact on the material depends on the intensity of the radiation. At normal doses (typically 2.5 to 10 GGy) for sterilisation purposes materials like silicone, polycarbonates, polyacrylates and polyesters form some free radicals, but the number of free radicals formed is not high enough so as to destroy the material or its suitability for medical use. However, the free radicals can lead to discoloration.

If the exposure to radiation takes place in the presence of oxygen, the discoloration is usually not too pronounced, as oxygen is capable of quickly scavenging the free radicals and, thus, prevent the formation of coloured species. However, there is also a demand for conducting the radiation sterilization process in the absence of oxygen. This is particularly true for complicated parts like kidney dialyzer housings and sensitive filter elements.

In the absence of air and thus oxygen, the radicals formed in the polymeric material are no longer scavenged or quenched and thus they tend to form conjugated radicals, which eventually form temporarily or permanently coloured species. This is rather undesirable, as it largely imparts the appearance of the sterilized item. In the field of medical devices, this discoloration is particularly undesirable as physicians would prefer as little color as possible so as to e.g. assess the real color of a fluid such as blood contained in the article. Furthermore, a yellow color is inacceptable from an aesthetic standpoint because it is regarded as an indication of an "old" or "used" article.

Prior art attempts to address this problem have resulted in mixtures of polypropylene glycol and polymer materials, such as polycarbonates. In this regard reference is made to U.S. Pat. No. 4,904,710. The addition of polypropylene glycol has been partially successful. However, polypropylene glycol has a limited effect and it reduces discoloration only very slowly (up to 65 days). This is not an acceptable time frame for many users, not least as it entails an increased inventory and thus higher costs. Prior art efforts have thus been directed to alternative means, such as those disclosed in DE 195 42 186, EP 0 152 012 and EP 0 611 797.

Especially the latter application considers the use of a sulphur-containing compound, preferably a dithionate in combination with a polyalcohol, so as to reduce discoloration of polycarbonate resins during irradiation. This reference uses large amounts of thio compounds, yet the results are still not satisfactory. This is especially true for compositions containing monothionates as opposed to dithionates. It in fact turns out that contrary to the disclosure of EP-A 0 611 797, compositions containing monothionates do not show any improvement over compositions containing no such compound. This is at least true for compositions containing small amounts of thionates such as 0.5% or less.

BRIEF DESCRIPTION OF THE SEVERAL VIEWS OF THE DRAWING FIGURES

Figure 2:
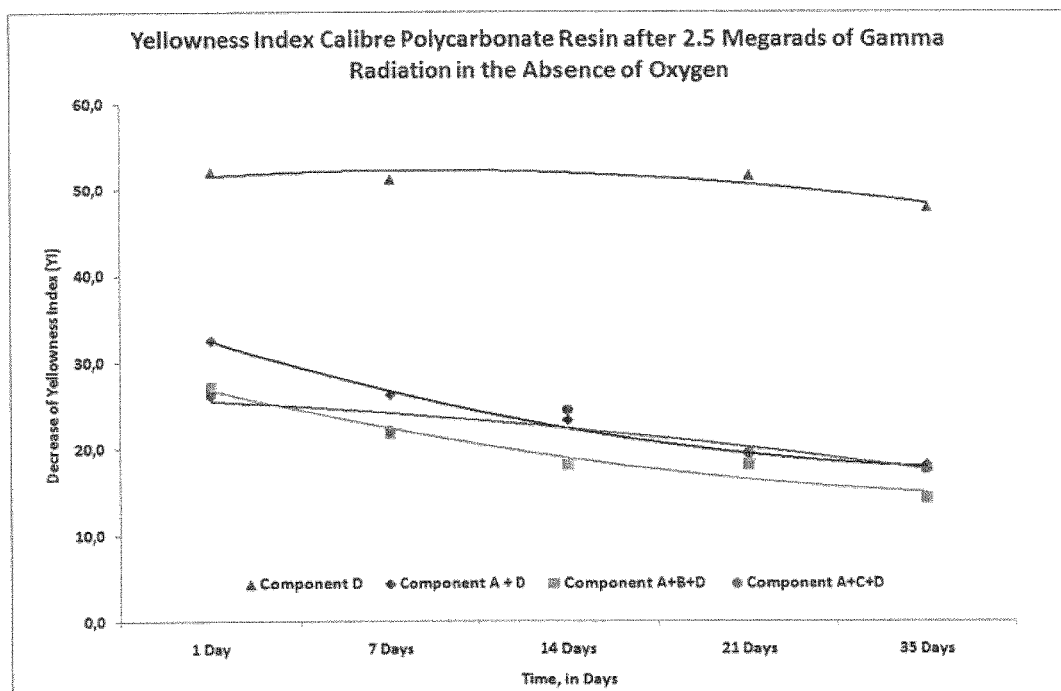

FIG. 1 shows a graph depicting yellowness index of calibre polycarbonate resin after 2.5 megarads of gamma radiation in air over a length of several days; and FIG. 2 shows a graph depicting yellowness index of calibre polycarbonate resin after 2.5 megarads of gamma radiation in the absence of oxygen over a length of several days.

It is thus an object underlying the present invention to provide an improved composition for scavenging radicals and/or reducing yellowing of polymeric materials. The present invention in particular aims at a composition that reduces discoloration quickly and leads to low overall yellowing. The present invention is beneficial both in the presence and absence of oxygen. Its effect is particularly pronounced in the absence of oxygen.

In order to meet this object, the present invention proposes to use a mixture of a polyalkylene glycol and a thio compound with the following formula (I):

wherein:
 $R^1$ is a straight chain, branched or cyclic alkyl group with 1 to 24 carbon atoms,
 n is an integer from 1 to 6,
 m is an integer of 1 to 16,
 p is 1 or 0,
 A is an oxygen or sulphur atom,
 q is 1 or 0, and
 $R^2$ is a straight chain, branched or cyclic alkyl group with 1 to 24 carbon atoms.

It has been found that the combination of a polyalkylene glycol with the above thio compound leads to particularly low levels of yellowing and discoloration, when added to polymeric materials, such as aromatic polycarbonates, which are subjected to high energy radiation sterilization in the presence or absence of oxygen.

The thio compound according to the present invention is defined by formula (I):

wherein:
 $R^1$ is a straight chain, branched or cyclic alkyl group with 1 to 24 carbon atoms,
 n is an integer from 1 to 6,
 m is an integer of 1 to 16,
 p is 1 or 0,
 A is an oxygen or sulphur atom,
 q is 1 or 0, and
 $R^2$ is a straight chain, branched or cyclic alkyl group with 1 to 24 carbon atoms.

Preferable thio compounds are compounds with formula (I):

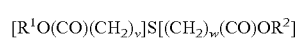

wherein v and w are independently integers from 1 to 6, and $R^1$ and $R^2$ are independently straight chain, branched or cyclic alkyl groups with 1 to 24 carbon atoms.

In a most preferred embodiment, v and w represent integers of less than 4, preferably 2. The most preferred groups for $R^1$ and $R^2$ are straight chain alkyl groups with 8 to 24 and most preferred 12 to 18 carbon atoms.

One highly preferential compound is obtained when both v and w represent 2 and $R^1$ and $R^2$ represent a $C_{12}$ or $C_{16}$ straight chain alkyl group.

The polyalkylene glycol compound according to the present invention can be chosen from a wide variety of glycols, such as glycols covered by formula (III):

$$R^4O-[C(R^5)H-C(R^5)H]_r-[O-C(R^5)H-C(R^5)H-]_sOR^4$$

wherein:

$R^4$ is independently hydrogen or a straight chain, branched or cyclic alkyl group with 1 to 24, preferably 1 to 12 or 1 to 6 carbon atoms, $R^5$ is independently hydrogen, methyl or ethyl, r and s are independently represent integers from 1 to 2000, such as 1 to 1000, preferably 5 to 500, such as 5 to 50.

Preferred polyalkylene glycols are polyethylene glycol, polypropylene glycol, polybutylene glycol, polyhexylene glycol as well as poly(THE) glycol. Polypropylene glycol is particularly preferred.

In a most preferred embodiment, the polypropylene glycol is a compound of formula (IV):

wherein t and u may independently represent integers from 5 to 30, preferably 10 to 20. In the most preferred embodiment r represents 15 and s represents 16.

The polyalkylene glycol according to the present invention preferably has an average molecular weight ($M_w$) in the range of 200 to 4000 g/mol, preferably 300 to 3000 g/mol such as 500 to 2000 g/mol.

In the composition according to present invention the polyalkylene glycol and the thio compound may be used in a ratio of 1:1 to 50:1, preferably 30:1 or 20:1, more preferably 12:1.

It was found that already very small amounts of the thio compounds give good results. That is 2000 ppm or less, 1500 ppm or less, preferably 1000 ppm or less or even 850 ppm or less such as 500 ppm or even 50 ppm or less already produce a significant improvement. At the same time, it was found, that higher amounts of thio compounds are possible, but not necessarily beneficial.

The composition according to the present invention may be formulated as convenient for the purpose. For instance, one may melt the thio compound and blend it with the polyalkylene glycol in the liquid state. However, other standard methods such as extrusion are also possible.

If prepared in form of a liquid or solid formulation, the formulations may then be mixed with a polymeric component. In the alternative, it is also possible to mix the polyalkylene compound, the thio compound and the polymeric component, in any given order without preparing a separate formulation of the polyalkylene glycol and the thin compound.

The polymeric compound, to which the composition according to the present invention can be added, is not particularly limited. Polymeric materials that suffer from discoloration upon irradiation with high energy rays, such as gamma rays are preferred. Examples of such polymeric materials are transparent polymers comprising aromatic groups, such as acrylic polymers, polyesters and polyamides and in particular polycarbonates as well as co-polymers and polymer blends thereof. Preferred are polycarbonates, especially aromatic polycarbonates and polyesters as well as blends and copolymers thereof. Polycarbonates derived from bisphenol A are preferred within the context of the present invention.

When used with a polymeric material, the amounts of the compounds according to the present invention are as follows:

| | |
|---|---|
| polyalkylene glycol: | 5 wt.-% or less, preferably 3 wt. %, most preferably 0.5-1.5 wt.-%, such as 1 wt.-%; |
| thio compound: | 0.9 wt.-% or less based on the total weight of the composition; preferably 0.5 wt.-% or less; more preferably 0.2 wt.-% or 0.15 wt.-% or less, such as 0.005-0.01 wt.-%, e.g. 0.005-0.09 wt.-%, preferably 0.8-0.09 wt.-%, especially 0.085 wt.-% or less and |
| polymeric material: | 99.5 wt.-% or less, such as 5-99.5 wt.-%, preferably 30-99 wt.-% and most preferably 80-99 wt.-% |

The aforementioned percentages are all based on the total weight of the composition. The indicated ranges are to be construed as disclosing each and every value falling within the given ranges. They are merely abbreviated representations that should be construed as individualising each value within the range. Moreover, the aforementioned ranges must be construed as disclosing not only the individual values in each range but also as individualising any combination between the individual values from these ranges.

The polyalkylene/thio compound/polymeric material-containing composition according to the present invention may contain heat stabilizers like P168, triphenyl phosphine, phosphate stabilisers such as Weston 705 and the like; mold release agents; pigments; optical brighteners and other components.

The polymeric material containing composition according to the present invention can favourably be used for making medical devices that need to be sterilised, such as housings, blood reservoirs, reactors and the like.

The sterilization can be conducted in the presence or absence of oxygen. If sterilization by gamma radiation or other high energy radiation is effected in the presence or absence of oxygen, the composition according to the present invention suffers from considerably reduced discoloration.

EXAMPLES 1 TO 4

All formulations were prepared as follows: A total amount of 4.00 kg of material was prepared by adding the below indicated relative amounts of the compounds into a Henschel blender. The polycarbonate was added in form of ground pellets (powder), the polypropylene glycol was added as a liquid (oil), whereas the thio compounds were added as powders. The blending process took 3 min in order to prepare homogeneous mixtures.

| | | Example | | | |
|---|---|---|---|---|---|
| | | 1 | 2 | 3 | 4 |
| Polymeric material | bisphenol A-based polycarbonate | 100% | 99% | 98.914% | 98.871% |
| Polyalkylene glycol | polypropylene glycol (Synalox 100 D95) | | 1% | 1% | 1% |
| Thio compound | dioctadecyl 3,3'-thiodipropionate | | | 0.129% | |
| | didodecyl 3,3'-thiodipropionate | | | | 0.086% |

Weight percent rased on weight of entire composition

The resulting mixture was extruded and cut into pellets using a Brabender ZSK 25 extruder working at a melt temperature of 300° C. The obtained pellets were dried and injection molded on a Demag injection molding machine. The melt temperature was 300° C. while the mold had a temperature of 90° C. Optical chips of 3.2×30×80 mm were made and the optical measurements were carried out according to ASTM D 1925

Then the chips were subjected to gamma radiation (2.5 GGy). The radiation was used in an air- and oxygen-free atmosphere. The yellowness index was measured after 1, 7, 14, 21 and 35 days after irradiation. The results shown in the Tables 1 and 2 are also shown in FIGS. 1 and 2.

TABLE 1

Gamma Radiation in air (Yellowing Index)

| Example No. | No Radiation | 1 Day | 7 Days | 14 Days | 21 Days | 35 Days |
|---|---|---|---|---|---|---|
| 1 | 1.61 | 20.15 | 16.56 | 14.86 | 14.17 | 13.93 |
| 2 | 1.34 | 14.19 | 10.34 | 9.86 | 9.74 | 9.76 |
| 3 | 1.08 | 11.15 | 8.97 | 8.62 | 8.51 | 8.48 |
| 4 | 1.23 | 11.43 | 8.85 | 8.47 | 8.31 | 8.27 |

TABLE 2

Gamma Radiation in absence of oxygen (Yellowing iodex)

| Example No. | No Radiation | 1 Day | 7 Days | 14 Days | 21 Days | 35 Days |
|---|---|---|---|---|---|---|
| 1 | 1.61 | 52.05 | 51.19 | 30.65* | 51.61 | 47.81 |
| 2 | 1.34 | 32.50 | 26.24 | 23.32 | 18.59 | 18.20 |
| 3 | 1.08 | 26.18 | 22.06 | 24.44 | 19.47 | 17.64 |
| 4 | 1.23 | 27.23 | 21.75 | 18.15 | 18.18 | 14.21 |

* Erroneous value, most likely due to oxygen penetration

EXAMPLES 5 TO 8

A second series of samples with varying concentrations of the thio compounds components was prepared and subjected to comparable irradiation conditions as documented in Tables 3 and 4. The storage time was reduced to 21 days which contains the most interesting time span of one to two weeks which is the desired target in the medical device market place.

| | | Example | | | |
|---|---|---|---|---|---|
| | | 5 | 6 | 7 | 8 |
| Polymeric material | bisphenol A-based polycarbonate | 98.838% | 98.967% | 98.914% | 99.871% |
| Polyalkylene glycol | polypropylene glycol (Synalox 100 D95) | 1% | 1% | 1% | 1% |
| Thio compound | dioctadecyl 3,3'-thiodipropionate | | | 0.215% | 0.043% |
| | didodecyl 3,3'-thiodipropionat | 0.162% | 0.033% | | |

Weight percent based on weight of entire composition

TABLE 3

Gamma Radiation in air (Yellowing Index)

| Example No. | No Radiation | 1 Day | 7 Days | 14 Days | 21 Days |
|---|---|---|---|---|---|
| 5 | 1.04 | 14.18 | 8.63 | 8.51 | 8.44 |
| 6 | 1.16 | 16.18 | 9.19 | 9.51 | 9.27 |
| 7 | 1.09 | 14.76 | 8.84 | 9.04 | 8.80 |
| 8 | 1.22 | 16.49 | 9.15 | 9.14 | 9.03 |

TABLE 4

Gamma Radiation in absence of oxygen (Yellowing index)

| Example No. | No Gamma | 1 Day | 7 Days | 14 Days | 21 Days |
|---|---|---|---|---|---|
| 5 | 1.04 | 30.17 | 24.00 | 10.73* | 18.56 |
| 6 | 1.16 | 31.84 | 24.30 | 20.21 | 18.98 |
| 7 | 1.09 | 31.98 | 24.30 | 12.21* | 20.66 |
| 8 | 1.22 | 31.55 | 23.36 | 21.77 | 18.57 |

*Erroneous value, most likely due to oxygen penetration

The second series was subjected to comparable albeit not identical irradiation conditions. The radiation dose was a little higher as can be inferred from the overall higher yellowing index values after 1 day (with and without oxygen).

As can be seen from tables 3 and 4, the change of concentration of the thio components did not result in a significant change of the additives effectiveness—even at very low concentrations. The present invention therefore allows to use much lower amounts of sulphur-containing compounds as compared to the prior art.

EXAMPLES 9 TO 17

Comparative

In a third series the effect of an alkylglycol and a thiocompond as separate additives was investigated in the absence of oxygen (wt.-%)

| Day Ex. | bisphenol A-based PC | polypropylene glycol (Synalox 100 D95) | dioctadecyl 3,3'-thiodipropionate | 1 | 7 | 14 | 21 |
|---|---|---|---|---|---|---|---|
| 9 | 100.00 | 0 | 0 | 52.05 | 51.19 | 30.65 | 51.61 |
| 10 | 99.75 | 0.25 | 0 | 45.06 | 41.05 | 34.39 | 34.26 |
| 11 | 99.50 | 0.50 | 0 | 39.96 | 33.86 | 29.29 | 28.13 |
| 12 | 99.00 | 1.00 | 0 | 32.50 | 26.24 | 23.32 | 18.59 |

-continued

| Ex. | Day bisphenol A-based PC | polypropylene glycol (Synalox 100 D95) | dioctadecyl 3,3'-thiodipropionate | 1 | 7 | 14 | 21 |
|---|---|---|---|---|---|---|---|
| 13 | 99.914 | 0 | 0.086 | 53.00 | 48.95 | 48.03 | 47.36 |
| 14 | 99.829 | 0 | 0.171 | 52.57 | 49.78 | 49.13 | 47.86 |
| 15 | 99.658 | 0 | 0.342 | 52.75 | 48.96 | 47.93 | 46.20 |

This data clearly shows that while the addition of the thio compound alone does not lead to a significant improvement over the PC material without any additives. The polypropylene glycol on the other hand does lead to some improvement. Bearing this in mind, it is entirely surprising that the combination according to the present invention leads to an improvement over the use of PPG alone.

The invention claimed is:

1. A method of sterilizing a medical device, comprising: exposing the medical device to about 2.5 GGy or more of gamma radiation, wherein the medical device comprises a composition, the composition comprising about 99% bisphenol A-derived polycarbonate, about 1% polypropylene glycol, and about 0.13% dioctadecyl 3,3'-thiodipropionate.

2. The method of claim 1, wherein the exposing step is carried out in an oxygen-free atmosphere.

3. A composition comprising about 99% bisphenol A-derived polycarbonate, about 1% polypropylene glycol, and about 0.13% dioctadecyl 3,3'-thiodipropionate.

* * * * *